United States Patent
Argembeaux et al.

(10) Patent No.: US 8,603,450 B2
(45) Date of Patent: Dec. 10, 2013

(54) SHOWER AND SHAVE PREPARATION

(75) Inventors: Horst Argembeaux, Wentorf (DE); Miriam Belser, Hamburg (DE); Katrin Counradi, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1027 days.

(21) Appl. No.: 12/258,983

(22) Filed: Oct. 27, 2008

(65) Prior Publication Data
US 2009/0162310 A1 Jun. 25, 2009

(30) Foreign Application Priority Data
Dec. 20, 2007 (DE) .......................... 10 2007 062 427

(51) Int. Cl.
A61Q 9/02 (2006.01)
A61Q 5/02 (2006.01)
A61Q 5/12 (2006.01)
A61K 8/44 (2006.01)
A61K 8/46 (2006.01)

(52) U.S. Cl.
USPC .... 424/73; 424/70.11; 424/70.17; 424/70.21; 424/70.24; 424/401

(58) Field of Classification Search
None
See application file for complete search history.

(56) References Cited

U.S. PATENT DOCUMENTS

| | | | |
|---|---|---|---|
| 5,911,981 A | 6/1999 | Dahms et al. | |
| 5,976,520 A | 11/1999 | Babinski et al. | |
| 5,993,792 A * | 11/1999 | Rath et al. | 424/70.28 |
| 6,107,352 A | 8/2000 | Zofchak et al. | |
| 6,338,842 B1 * | 1/2002 | Restle et al. | 424/70.1 |
| 6,451,300 B1 * | 9/2002 | Dunlop et al. | 424/70.27 |
| 6,525,034 B2 * | 2/2003 | Dalrymple et al. | 514/77 |
| 2005/0158269 A1 * | 7/2005 | Simonet | 424/70.21 |
| 2005/0189377 A1 | 9/2005 | Lanzendorfer et al. | |
| 2005/0201967 A1 | 9/2005 | Albrecht et al. | |
| 2008/0118456 A1 * | 5/2008 | Brautigam et al. | 424/70.13 |

FOREIGN PATENT DOCUMENTS

| | | |
|---|---|---|
| AU | B-41853/93 | 7/1995 |
| DE | 43 24 358 | 1/1994 |
| DE | 199 37 916 | 2/2001 |
| DE | 103 10 381 | 9/2004 |
| DE | 10 2005 044 663 | 1/2007 |
| EP | 1 537 856 | 6/2005 |
| JP | 63-132817 | 6/1988 |
| JP | 63-308097 | 12/1988 |
| JP | 2006-96754 | 4/2006 |
| WO | 97/25975 | 7/1997 |

OTHER PUBLICATIONS

International Cosmetic Ingredient Dictionary and Handbook, seventh edition, vol. 2, pp. 1654-1655 (1997).*
English Language Abstract of DE 103 10 381.
English Language Abstract of DE 199 37 916.
English Language Abstract of JP 63-132817.
English Language Abstract of JP 63-308097.
English Language Abstract of JP 2006-96754.
English Language Abstract of DE 10 2005 044 663.

* cited by examiner

Primary Examiner — Daniel Sullivan
Assistant Examiner — Barbara Frazier
(74) Attorney, Agent, or Firm — Abel Law Group, LLP

(57) ABSTRACT

A cosmetic cleansing and shaving preparation which comprises a surfactant system of (i) one or more amphoteric surfactants and (ii) one or more anionic surfactants, the weight ratio (i):(ii) being greater than about 1:1. This Abstract is not intended to define the invention disclosed in the specification, nor intended to limit the scope of the invention in any way.

16 Claims, No Drawings

SHOWER AND SHAVE PREPARATION

CROSS-REFERENCE TO RELATED APPLICATIONS

The present application claims priority under 35 U.S.C. §119 of German Patent Application No. 10 2007 062 427.3, filed Dec. 20, 2007, the entire disclosure of which is expressly incorporated by reference herein.

BACKGROUND OF THE INVENTION

1. Field of the Invention

The present invention relates to a shower and shave preparation which comprises amphoteric and anionic surfactants.

2. Discussion of Background Information

The daily hygiene routines for many consumers of both sexes include showering and, for men, shaving their beards. However, shaving certain areas of the body, such as, e.g., legs and armpits, is widespread among female consumers and increasingly among male consumers as well.

Commercially available shower preparations, such as shower gel, shower emulsions or shower oils are generally used for showering. For shaving, if it is a wet shave, foamable or self-foaming soaps, gels or foams are used to prepare for the shaving process with the razor blade.

Since many consumers shave in combination with showering before or afterwards, for them it would be a great advantage to have a product available that supports both processes equally. However, if a shower product according to the prior art is used for shaving, one realizes that this process is very uncomfortable. The quantity of the foam and in particular the stability of the foam is not adequate to be able to distribute it over the shaving area and for it to remain there through the end of shaving. The consistency of the foam is not compact enough either to exert a damping effect on the razor; moreover, the foam also tends to flow away quickly. If the razor is drawn over the shaving area, one feels an inadequate gliding, which leads to unpleasant tugging and in extreme cases to cuts.

If a shaving product is used for showering, it is noticeable that it is hard to distribute over the entire body due to the compact foam. Since such products are usually formed on a soap basis, their tolerability is much worse than that of normal shower gels, the acid-base balance of the skin is disturbed. This can burn unpleasantly and itch in particular in the area of the mucous membranes or lead to redness or even to the formation of erythemas. Another disadvantage is that it is difficult to rinse off the skin.

Shower gels with good foaming properties are known. Thus, for example, DE 102005033663, the entire disclosure whereof is incorporated by reference herein, discloses cosmetic cleansing preparations comprising anionic sulfuric acid esters, an amphoteric surfactant, ethoxylated glycerol fatty acid esters with 3 to 12 EO units, wherein the content of ethoxylated glycerol fatty acid esters is higher than 1.2%, and the content of surfactants is in total lower than 16 wt. %, wherein ethoxylated glycerol fatty acid esters with 3 to 12 EO units are also to be counted as surfactants. These are shower gels that comprise at a low total surfactant concentration a higher proportion of amphoteric surfactants than of anionic surfactants and thus are particularly mild. However, for a good shaving process, foams of this type lack a certain adhesive strength, furthermore, products of this type do not exhibit gliding properties suitable for shaving.

The prior art therefore lacks preparations that combine the advantages of a shower gel with those of a shaving product without exhibiting its disadvantages.

It was surprisingly found that a cosmetic cleansing and shaving preparation with a surfactant system of amphoteric surfactant and anionic surfactant and a ratio of amphoteric to anionic surfactant of greater than about 1 remedies the disadvantages of the prior art and is extremely suitable as the basis for a shower and shave product.

SUMMARY OF THE INVENTION

The present invention provides a cosmetic cleansing and shaving preparation. The preparation comprises a surfactant system of (i) one or more amphoteric surfactants and (ii) one or more anionic surfactants, the weight ratio (i):(ii) being greater than about 1:1.

In one aspect of the preparation, the weight ratio may be at least about 1.3:1, e.g., at least about 1.5:1.

In another aspect, the preparation may comprise (i) and (ii) in a total concentration of at least about 5% by weight and/or of not more than about 25% by weight, based on the total weight of the preparation.

In yet another aspect, component (i) may comprise cocoamidopropyl betaine and/or component (ii) may comprise at least one lauryl ether sulfate (such as, e.g., sodium lauryl ether sulfate).

In a still further aspect, the preparation may further comprise one or more ethoxylated fatty acid esters in a concentration of not more than about 3% by weight, based on a total weight of the preparation. For example, the one or more ethoxylated fatty acid esters may be present in a concentration of at least about 0.05% by weight and/or may comprise one or more glycerol fatty acid esters having a carbon chain length of from about 10 to about 22 such as, e.g., PEG-7 glyceryl cocoate.

In another aspect, the preparation of the present invention may further comprise a combination of one or more cationic polymers and one or more nonionic polymers such as, e.g., a combination of polyquatemium-7 and PEG-90M. For example, polyquaternium-7 and PEG-90M may be present in a total concentration of from about 0.1% to about 1% by weight.

In another aspect, the preparation of the present invention may comprise components (i) and (ii) in a total concentration of from about 8% to about 16% by weight, based on a total weight of the preparation and/or may comprise from about 0.05% to about 3% by weight of one or more ethoxylated fatty acid esters which comprise one or more glycerol fatty acid esters having a carbon chain length of from about 10 to about 22 and/or may further comprise a combination of one or more cationic polymers and one or more nonionic polymers.

The present invention also provides a method of improving the razor gliding ability and foam adhesion of a cosmetic cleansing preparation which comprises one or more cationic surfactants and one or more nonionic surfactants. The method comprises incorporating into the preparation a surfactant system of (i) one or more amphoteric surfactants and (ii) one or more anionic surfactants, the weight ratio (i):(ii) being greater than about 1:1.

The present invention also provides a method of improving the cleansing ability, mildness and ease of distribution and rinsing of a shaving preparation which comprises one or more cationic surfactants and one or more nonionic surfactants. The method comprises incorporating into the preparation a surfactant system of (i) one or more amphoteric surfactants and (ii) one or more anionic surfactants, the weight ratio (i):(ii) being greater than about 1:1.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice. Unless stated otherwise, all amounts, fractions and percentages given are based on the weight and the total amount or on the total weight of the preparations.

It is particularly preferred when a surfactant system of cocamidopropyl betaine and lauryl ether sulfates is used. This surfactant system is further improved by additional contents up to about 3% by weight, but usually not less than about 0.01% by weight of ethoxylated fatty acid esters, in particular fatty acid glycerol esters with a carbon chain length of about 10-22. PEG-7 glyceryl cocoate is a particularly suitable ester. Surfactant systems of this type exhibit excellent foam properties. It is particularly preferred when a combination of one or more cationic polymers and one or more nonionic polymers is additionally contained in the preparation. A combination of polyquatemium-7 and PEG-90 M is particularly preferred. An improved gliding ability with a compact foam with good adhesive strength but without a sticky feel can thus be achieved without stringy products or sticky foams being obtained.

The total concentration of the one or more amphoteric surfactants and the one or more anionic surfactants in the preparation of the present invention usually is at least about 5%, e.g., at least about 8%, at least about 10%, or at least about 11% by weight, but usually not higher than about 25%, e.g., not higher than about 20%, not higher than about 18%, or not higher than about 16% by weight, based on the total weight of the preparation.

The preparation of the present invention will further usually comprise a substantial amount of water, e.g., at least about 50%, at least about 60%, at least about 70%, or at least about 80% by weight of water, based on the total weight of the preparation.

Surprisingly, it was also found that systems of the type used in the present invention reduce the cutting force of hairs. It was shown that compared to shower gel formulations not according to the present invention, the preparations according to the present invention can significantly reduce the force for severing an individual hair with the aid of a razor blade.

The invention also encompasses the use of a surfactant system as described above with a combination of cationic polymers and nonionic polymers as described above for improving the razor gliding ability and foam adhesive strength of a cosmetic cleansing preparation or also to improve the cleansing capacity, mildness, spreadability and rinsability of a shaving preparation.

Products with the surfactant systems and polymer systems described exhibit a good cleansing capacity, are mild and easy to distribute and to rinse off. They have a compact foam that adheres well and exhibit a good gliding ability. Skin treated with products of this type can be shaved very well and feels well-groomed.

EXAMPLES

|  | Example No. | | | | | | | |
| --- | --- | --- | --- | --- | --- | --- | --- | --- |
|  | 1 | 2 | 3 | 4 | 5 | 6 | 7 | 8 |
| Sodium lauryl ether sulfate | 5.5 | 4.5 | 4.0 | 3.5 | 4.5 | 4.0 | 4.5 | 5.0 |
| Cocoamidopropyl betaine | 9.0 | 9.0 | 8.0 | 8.0 | 7.0 | 7.0 | 9.0 | 10 |
| PEG-7 glyceryl cocoate | 1.0 | 1.5 | 2.0 | — | 1.5 | 2.5 | 2.0 | — |
| PEG-90 M | 0.05 | 0.1 | 0.05 | 0.05 | 0.075 | 0.03 | 0.1 | 0.075 |
| Polyquaternium-7 | 0.3 | 0.4 | 0.4 | 0.2 | 0.40 | 0.5 | 0.35 | 0.3 |
| PEG-3 distearate | 1.2 | 1.5 | — | 1.5 | 1.5 | 1.2 | 1.2 | 1.5 |
| PEG-200 hydrogenated glyceryl palmitate | 1.0 | 0.4 | 0.8 | 1.0 | 0.8 | 0.2 | 0.5 | 0.5 |
| PEG-200 hydrogenated castor oil | 0.7 | 0.6 | 0.4 | 0.3 | 0.6 | 0.4 | 0.5 | 0.6 |
| Panthenol | — | — | — | — | — | — | 0.1 | — |
| Soybean oil | — | 0.2 | — | — | — | — | — | — |
| Carica papaya | — | — | — | — | — | — | — | 0.1 |
| Sodium chloride | 0.3 | — | 0.3 | 0.3 | 0.1 | — | — | — |
| Sodium salicylate | 0.4 | 0.4 | 0.3 | 0.4 | 0.40 | 0.4 | 0.45 | 0.3 |
| Sodium benzoate | 0.4 | 0.5 | 0.5 | 0.4 | 0.45 | 0.4 | 0.4 | 0.4 |
| Citric acid | q.s. | q.s | q.s | q.s | q.s | q.s | q.s | q.s |
| Perfume | q.s | q.s | q.s | q.s | q.s | q.s | q.s | q.s |
| Water | ad 100 | ad 100 | ad 100 | ad 100 | ad 100 | ad 100 | ad 100 | ad 100 |

The weight ratio of the one or more amphoteric surfactants to the one or more anionic surfactants in the preparation of the present invention usually is at least about 1.1:1, e.g., at least about 1.2:1, or at least about 1.3:1, but is usually not higher than about 5:1, e.g., not higher than about 4:1, not higher than about 3:1, or not higher than about 2.5:1.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic cleansing and shaving preparation, wherein the preparation comprises at least about 5% by weight of a surfactant system of (i) one or more amphoteric surfactants which comprise cocoamidopropyl betaine and (ii) one or more anionic surfactants which comprise at least one lauryl ether sulfate, a weight ratio (i):(ii) being greater than about 1.5:1, and further comprises from about 0.05% to about 3% by weight of two or more ethoxylated fatty acid esters which comprise glycerol fatty acid esters having a carbon chain length of from about 10 to about 22 and comprise PEG-7 glyceryl cocoate and PEG-200 hydrogenated glyceryl palmitate, each based on a total weight of the preparation.

2. The preparation of claim 1, wherein the two or more ethoxylated fatty acid esters further comprise PEG-200 hydrogenated castor oil.

3. The preparation of claim 1, wherein the preparation further comprises a combination of one or more cationic polymers and one or more nonionic polymers.

4. The preparation of claim 3, wherein the preparation comprises polyquaternium-7 and PEG-90M.

5. The preparation of claim 4, wherein the preparation comprises polyquaternium-7 and PEG-90M in a total concentration of from about 0.1% to about 1% by weight.

6. The preparation of claim 1, wherein the preparation comprises (i) and (ii) in a total concentration of from about 8% to about 16% by weight, based on a total weight of the preparation.

7. A cosmetic cleansing and shaving preparation, wherein the preparation comprises from about 8% to about 18% by weight of a surfactant system of (i) one or more amphoteric surfactants which comprise cocoamidopropyl betaine and (ii) one or more anionic surfactants which comprise at least one lauryl ether sulfate, a weight ratio (i):(ii) being greater than about 1.5:1 but not higher than about 3:1, from about 0.05% to about 3% by weight of two or more ethoxylated fatty acid esters which comprise glycerol fatty acid esters having a carbon chain length of from about 10 to about 22 and comprise PEG-7 glyceryl cocoate and PEG-200 hydrogenated glyceryl palmitate, and a combination of one or more cationic polymers and one or more nonionic polymers, each based on a total weight of the preparation.

8. The preparation of claim 7, wherein the two or more ethoxylated fatty acid esters comprise PEG-7 glyceryl cocoate in a concentration of from 1.0% to 2.5% by weight.

9. The preparation of claim 8, wherein the two or more ethoxylated fatty acid esters further comprise PEG-200 hydrogenated castor oil in a concentration of from 0.3% to 0.7% by weight.

10. The preparation of claim 7, wherein the preparation comprises polyquaternium-7 and PEG-90M.

11. The preparation of claim 10, wherein the preparation comprises polyquaternium-7 and PEG-90M in a total concentration of from about 0.1% to about 1% by weight.

12. A cosmetic cleansing and shaving preparation, wherein the preparation comprises from about 11% to about 16% by weight of a surfactant system of (i) one or more amphoteric surfactants which comprise cocoamidopropyl betaine and (ii) one or more anionic surfactants which comprise at least one lauryl ether sulfate, a weight ratio (i):(ii) being greater than about 1.5:1 but not higher than about 2.5:1, from about 0.05% to about 3% by weight of two or more ethoxylated fatty acid esters which comprise glycerol fatty acid esters having a carbon chain length of from about 10 to about 22 and comprise PEG-7 glyceryl cocoate and PEG-200 hydrogenated glyceryl palmitate, and from about 0.1% to about 1% by weight of a combination of polyquaternium-7 and PEG-90M, each based on a total weight of the preparation.

13. The preparation of claim 12, wherein the two or more ethoxylated fatty acid esters comprise PEG-7 glyceryl cocoate in a concentration of from 1.0% to 2.5% by weight.

14. The preparation of claim 12, wherein the two or more ethoxylated fatty acid esters further comprise PEG-200 hydrogenated castor oil in a concentration of from 0.3% to 0.7% by weight.

15. The preparation of claim 7, wherein the preparation further comprises sodium salicylate and sodium benzoate.

16. The preparation of claim 12, wherein the preparation further comprises sodium salicylate and sodium benzoate in a total concentration of up to 0.85% by weight.

* * * * *